(12) United States Patent
Bogner et al.

(10) Patent No.: US 10,456,048 B2
(45) Date of Patent: Oct. 29, 2019

(54) IMPLANTABLE SENSOR DEVICE ADAPTED TO SENSE A CHARACTERISTIC OF A BODY IN VIVO

(71) Applicant: Infineon Technologies AG, Neubiberg (DE)

(72) Inventors: Peter Bogner, Wernberg (AT); Dirk Hammerschmidt, Villach (AT)

(73) Assignee: Infineon Technologies AG (DE)

( * ) Notice: Subject to any disclaimer, the term of this patent is extended or adjusted under 35 U.S.C. 154(b) by 429 days.

(21) Appl. No.: 15/252,954

(22) Filed: Aug. 31, 2016

(65) Prior Publication Data

US 2017/0055850 A1    Mar. 2, 2017

(30) Foreign Application Priority Data

Aug. 31, 2015  (DE) .................. 10 2015 114 517

(51) Int. Cl.
*A61B 5/00* (2006.01)
*A61B 5/0215* (2006.01)
(Continued)

(52) U.S. Cl.
CPC .......... *A61B 5/02055* (2013.01); *A61B 5/002* (2013.01); *A61B 5/0031* (2013.01); *A61B 5/0205* (2013.01); *A61B 5/026* (2013.01); *A61B 5/0215* (2013.01); *A61B 5/0402* (2013.01); *A61B 5/0476* (2013.01);
(Continued)

(58) Field of Classification Search
CPC . A61B 5/02055; A61B 5/0402; A61B 5/0476; A61B 5/026; A61B 5/7246; A61B 5/002; A61B 5/0205; A61B 5/7225; A61B 5/0215; A61B 5/7278; A61B 5/0031; A61B 5/6876; A61B 2503/40; A61B 2562/0247;
(Continued)

(56) References Cited

U.S. PATENT DOCUMENTS

| 2002/0077553 | A1* | 6/2002 | Govari ................ A61B 5/0031 600/486 |
| 2003/0225318 | A1* | 12/2003 | Montegrande .......... A61B 3/16 600/300 |
| 2016/0220125 | A1* | 8/2016 | Karlovsky ........... A61B 5/0215 |

OTHER PUBLICATIONS

Zou, Xiaodan [et al.]: A 100-channel1-mW implantable neural recording IC. In: IEEE Transactions on circuits and systems 1: Regular papers, vol. 60, Nr. 10, Oct. 2013, S. 2584-2596.
(Continued)

*Primary Examiner* — Patricia Mallari
*Assistant Examiner* — Tho Q Tran
(74) *Attorney, Agent, or Firm* — Design IP

(57) ABSTRACT

A sensor device includes an implantable sensor unit, a transponder unit, and a wired connection flexibly and electrically connecting the implantable sensor unit and the transponder unit. The implantable sensor unit is adapted to be implanted into a body. The implantable sensor unit includes a comparator and a sensor adapted to sense a characteristic of the body in vivo. The sensor is adapted to supply an analog signal to a first input of the comparator. The transponder unit is adapted to supply a control signal to the implantable sensor unit and to receive an output signal of the comparator. The implantable sensor unit is adapted to supply an analog approximation signal to a second input of the comparator in response to the control signal. The wired connection is adapted to transmit the control signal and the output signal of the comparator.

22 Claims, 10 Drawing Sheets

(51) Int. Cl.
    *A61B 5/0205* (2006.01)
    *H03M 1/46* (2006.01)
    *A61B 5/026* (2006.01)
    *A61B 5/0402* (2006.01)
    *A61B 5/0476* (2006.01)

(52) U.S. Cl.
    CPC .......... *A61B 5/6876* (2013.01); *A61B 5/7225* (2013.01); *A61B 5/7246* (2013.01); *A61B 5/7278* (2013.01); *H03M 1/462* (2013.01); *A61B 5/0015* (2013.01); *A61B 2503/40* (2013.01); *A61B 2560/0209* (2013.01); *A61B 2562/028* (2013.01); *A61B 2562/0247* (2013.01)

(58) Field of Classification Search
    CPC ... A61B 2560/0209; A61B 5/021; A61B 5/02; H03M 1/462
    See application file for complete search history.

(56) References Cited

OTHER PUBLICATIONS

Cong, Peng [et al.]: Wireless batteryless implantable blood pressure monitoring microsystem for small laboratory animals. In: IEEE Sensors journal, vol. 10, Nr. 2, Feb. 2010, S. 243-254.

Van den Boom, Thomas [et al.]: Remote CMOS pressure sensor chip with wireless power and data transmission. In: Solid state circuits conference, 2000, Digest of technical papers, S. 186-188.

* cited by examiner

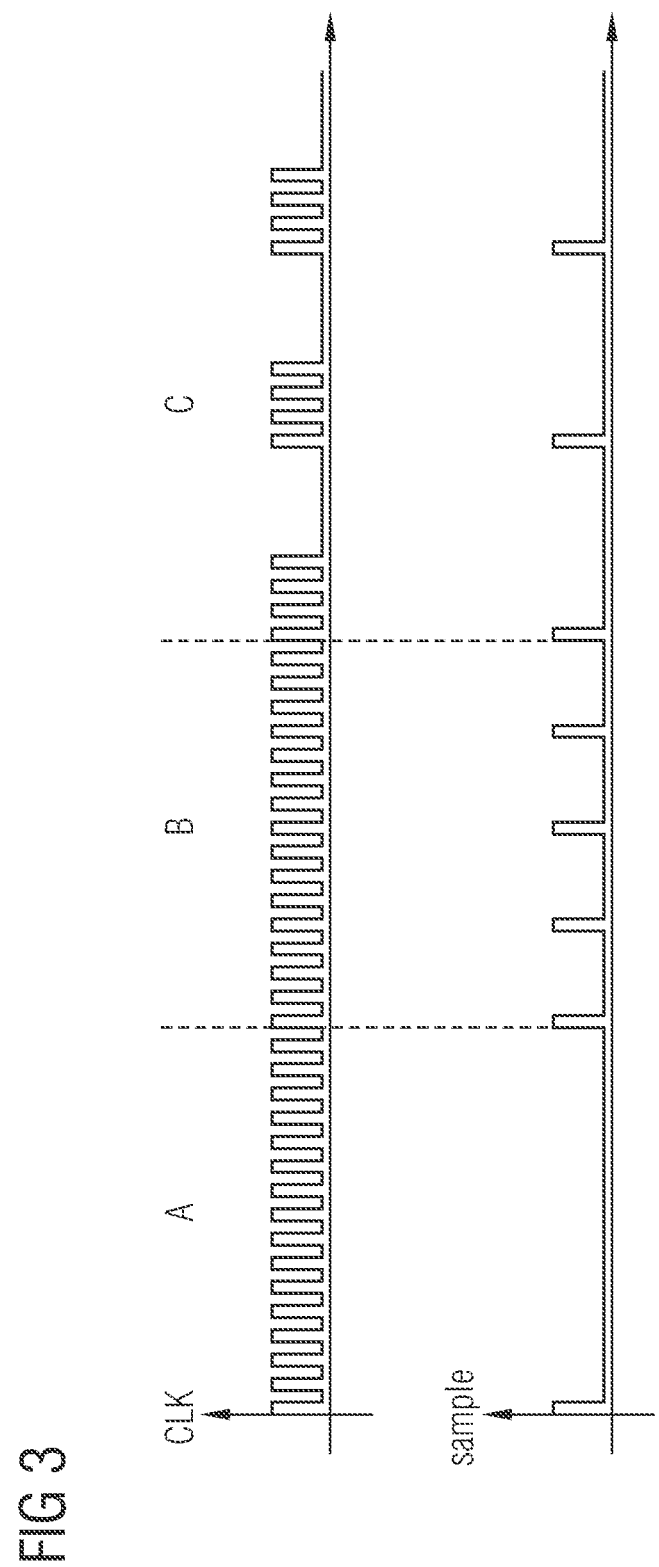

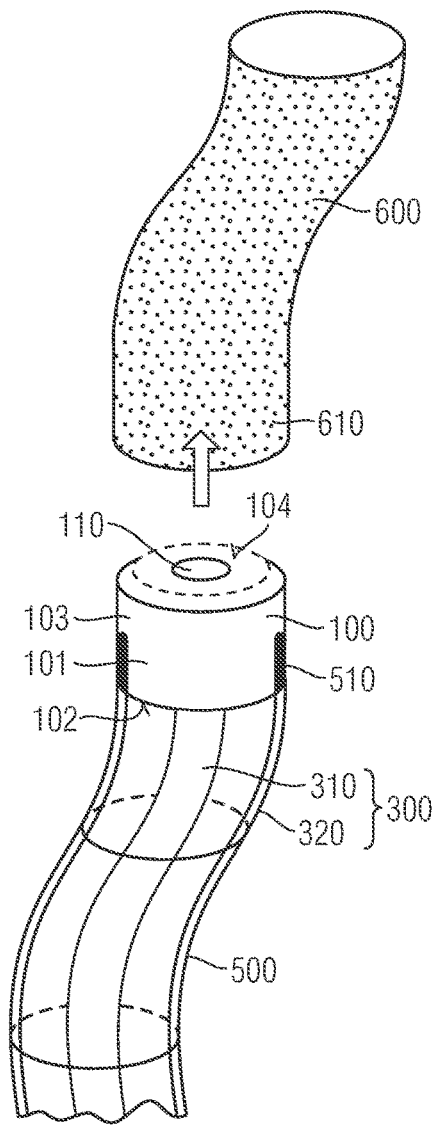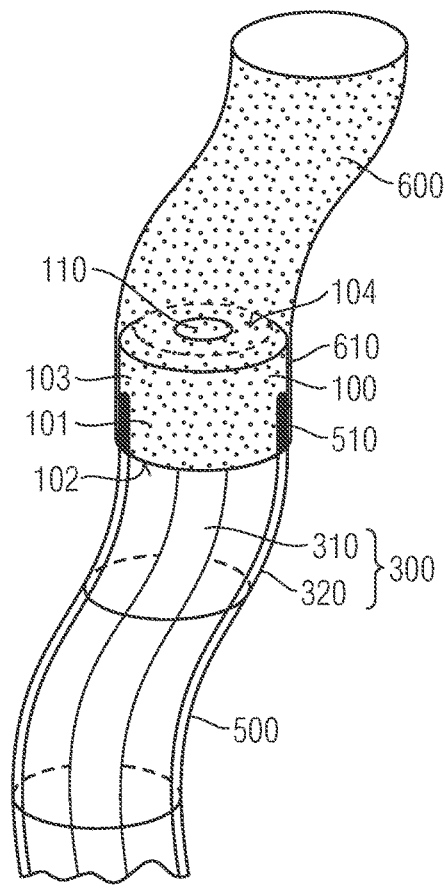

ns and methods, and, more particularly, to an implantable
IMPLANTABLE SENSOR DEVICE ADAPTED TO SENSE A CHARACTERISTIC OF A BODY IN VIVO

FIELD

The present disclosure relates generally to sensor devices and methods, and, more particularly, to an implantable sensors and methods adapted to sense a characteristic of a body in vivo.

BACKGROUND

Sensor devices may be employed for blood pressure sensing of rodents such as laboratory mice in medical studies. At present, blood pressure sensing is performed with a catheter that is connected to an external measurement equipment. The catheter is fluid filled and transfers the pressure mechanically. However, the blood pressure is quite inaccurate, since the system of the catheter adds a fluid pillar to the pressure and depends on the mouse body as well as the ambient temperature. It further forms a mechanical low pass that limits the dynamic of the signals. In addition, the mouse is tied to the external catheter tube, which causes massive stress to the mouse and thus reduces the value of the measured data. Finally the mouse often dies when the catheter is removed.

There are transponders existing that combine the catheter measurement principle with a wireless data link to avoid the external tube that hinders the mouse from normal activity. Those transponders still represent a large handicap for the mouse since the volume of the transponder is about 1 cm$^3$ and thus occupies a volume in the small animal that impacts its normal anatomy. The measurement suffers from the same problems as the catheter since it also uses the fluid filled tube to transfer the pressure from the blood vessel to the pressure sensor inside the transponder capsule, but due to the shorter catheter length the effect should be limited. Furthermore, the battery powered RF transponder has a limited lifetime which is severely shorter than the life of the animal and it has to be explanted for refurbishing due to its high price.

Therefore, it may be desired to provide a sensor device having an implantable sensor unit adapted to be easily implanted into a body and having a small size and low energy consumption.

SUMMARY

According to an embodiment of a sensor device, a sensor device includes an implantable sensor unit, a transponder unit, and a wired connection flexibly and electrically connecting the implantable sensor unit and the transponder unit. The implantable sensor unit is adapted to be implanted into a body. The implantable sensor unit includes a comparator and a sensor adapted to sense a characteristic of the body in vivo. The sensor is adapted to supply an analogue signal to a first input of the comparator. The transponder unit is adapted to supply a control signal to the implantable sensor unit and to receive an output signal of the comparator. The implantable sensor unit is adapted to supply an analogue approximation signal to a second input of the comparator in response to the control signal. The wired connection is adapted to transmit the control signal and the output signal of the comparator.

Those skilled in the art will recognize additional features and advantages upon reading the following detailed description and on viewing the accompanying drawings.

BRIEF DESCRIPTION OF THE DRAWINGS

The accompanying drawings are included to provide a further understanding of the general inventive concept and are incorporated in and constitute a part of this specification. The drawings illustrate the embodiments of the general inventive concept and together with the description serve to explain principles of the general inventive concept. Other embodiments and intended advantages will be readily appreciated as they become better understood by reference to the following detailed description.

FIG. 3 is a digital timing diagram illustrating a conversion sequence of an analogue signal of a sensor into digital sensor data according to one or more embodiments;

FIGS. 4A and 4B are schematic perspective views of an implantable sensor unit of a sensor device according to one or more embodiments before and after insertion into a vessel end;

DETAILED DESCRIPTION

In the following detailed description, reference is made to the accompanying drawings, which form a part hereof, and in which are shown by way of illustrations specific embodiments in which the general inventive concept may be practiced. It is to be understood that other embodiments may be utilized and structural or logical changes may be made without departing from the scope of the general inventive concept. For example, features illustrated or described for one embodiment can be used on or in conjunction with other embodiments to yield yet a further embodiment. It is intended that the general inventive concept includes such modifications and variations. The examples are described using specific language which should not be construed as limiting the scope of the appending claims. The drawings are not scaled and are for illustrative purposes only. For clarity, the same elements have been designated by corresponding references in the different drawings if not stated otherwise.

The terms "having", "containing", "including", "comprising" and the like are open and the terms indicate the presence of stated structures, elements or features but not preclude additional elements or features. The articles "a", "an" and "the" are intended to include the plural as well as the singular, unless the context clearly indicates otherwise.

The term "electrically connected" describes a permanent low-ohmic connection between electrically connected elements, for example a direct contact between the concerned elements or a low-ohmic connection via a metal and/or highly doped semiconductor. The term "electrically coupled" includes that one or more intervening element(s)

adapted for signal transmission may be provided between the electrically coupled elements, for example resistors, resistive elements or elements that are controllable to temporarily provide a low-ohmic connection in a first state and a high-ohmic electric decoupling in a second state.

Figure 1:
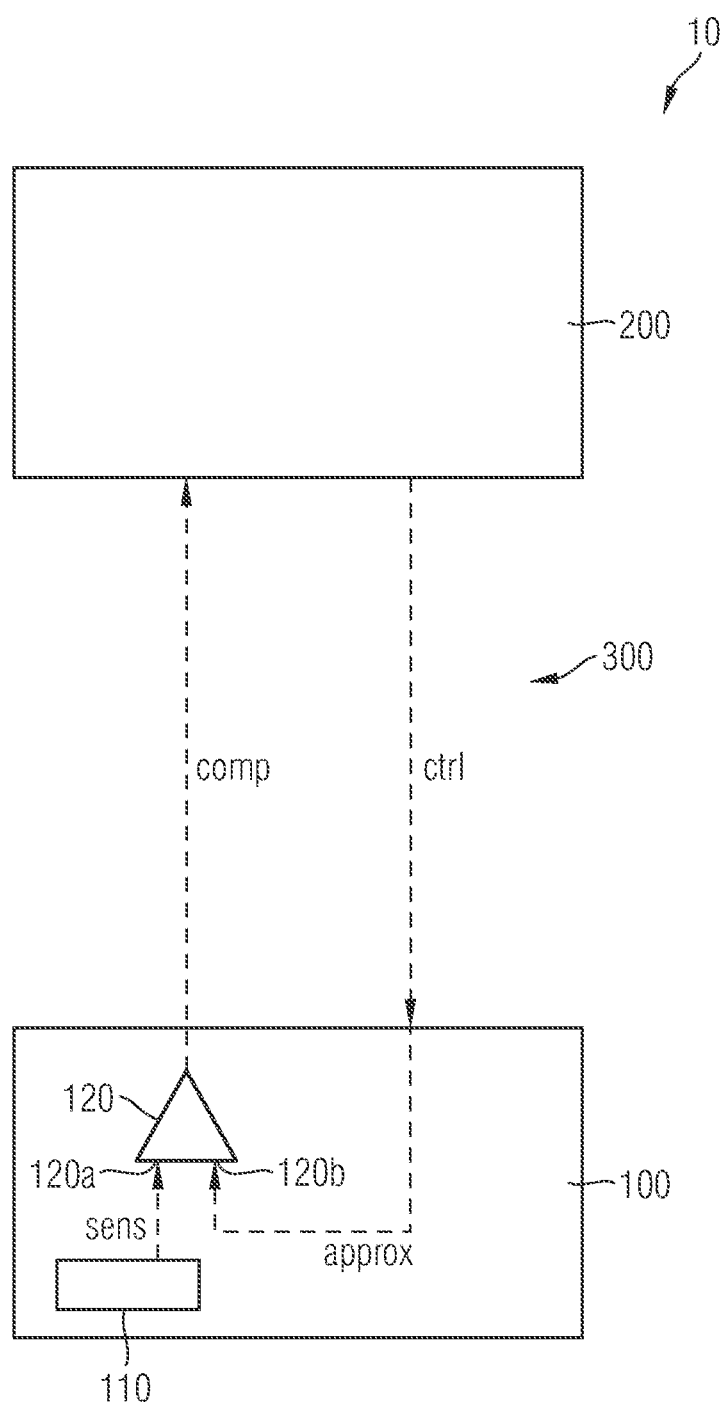
FIG. 1 is a schematic diagram of a sensor device according to one or more embodiments.

FIG. 1 is a schematic diagram of a sensor device 10 according to one or more embodiments. As can be seen from FIG. 1, the sensor device 10 comprises an implantable sensor unit 100, a transponder unit 200, and a wired connection 300 flexibly and electrically connecting the implantable sensor unit 100 and the transponder unit 200. The implantable sensor unit 100 is adapted to be implanted into a body. The implantable sensor unit 100 comprises a comparator 120 and a sensor 110 adapted to sense a characteristic of the body in vivo. The sensor 110 is adapted to supply an analogue signal sens to a first input 120a of the comparator 120. The transponder unit 200 is adapted to supply a control signal ctrl to the implantable sensor unit 100 and to receive an output signal comp of the comparator 120. The implantable sensor unit 100 is adapted to supply an analogue approximation signal approx to a second input 120b of the comparator 120 in response to the control signal ctrl. The wired connection 300 is adapted to transmit the control signal ctrl and the output signal comp of the comparator 120.

Since the control signal ctrl and the output signal comp of the comparator 120 are digital signals, the transmission reliability of the wired connection 300 between the implantable sensor unit 100 and the transponder unit 200 is enhanced while reducing, at the same time, the circuit size of the implantable sensor unit 100.

Figure 2:
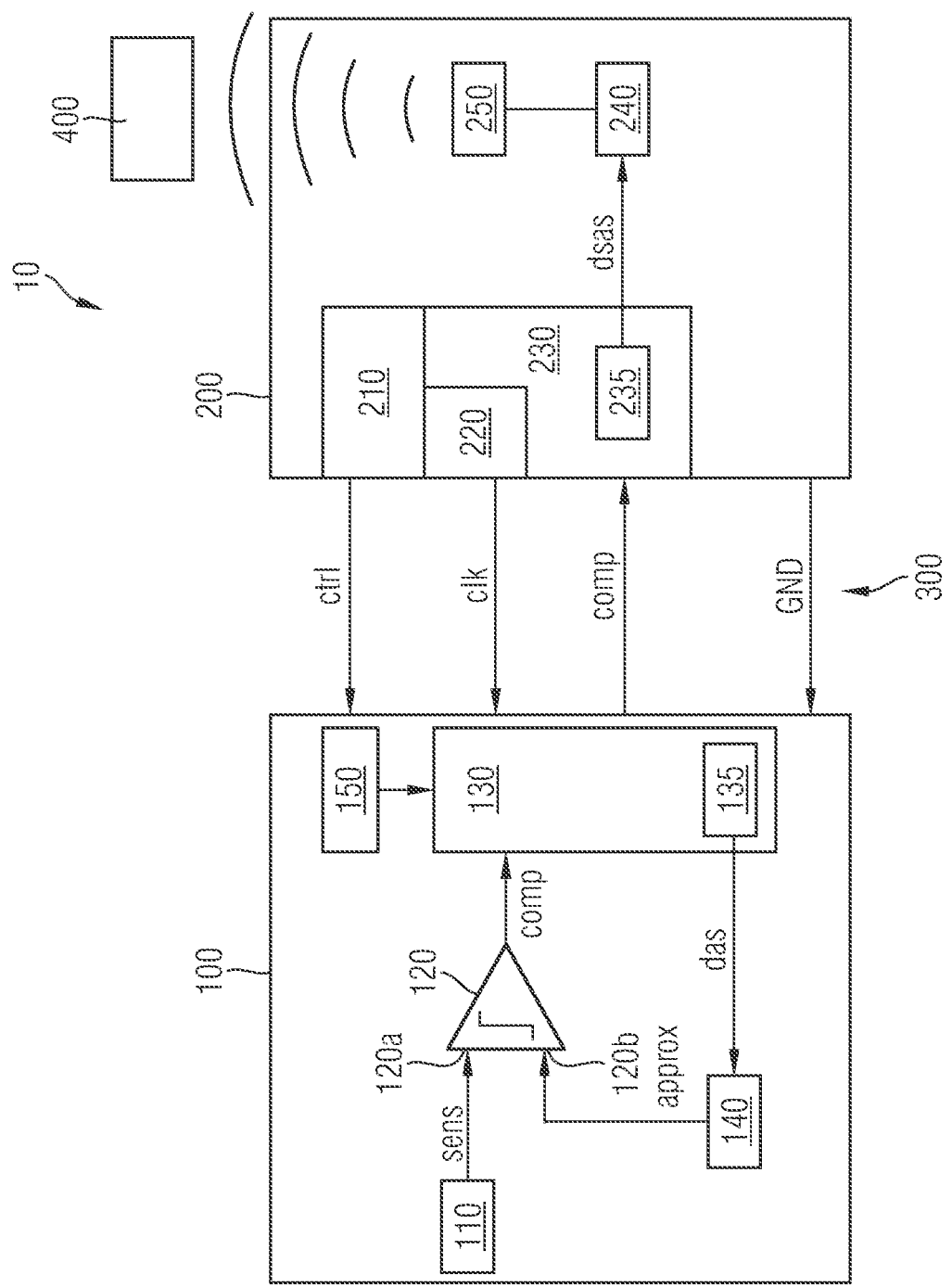
FIG. 2 is a schematic block diagram of a sensor device and an external reader according to one or more embodiments.

FIG. 2 is a schematic block diagram of a sensor device 10 and an external reader 400 according to one or more embodiments. As can be seen from FIG. 2, the sensor device 10 comprises an analogue-to-digital converting system, which is separated into two units, the implantable sensor unit 100 and the transponder unit 200. In detail, the implantable sensor unit 100 comprises the sensor 110, which supplies the analogue signal sens to the first input 120a of the comparator 120. The implantable sensor unit 100 further comprises a digital-to-analogue converter 140, which is adapted to supply the analogue approximation signal approx to the second input 120b of the comparator 120 based on a digital approximation signal das. In addition, the implantable sensor unit 100 comprises a state machine 130 including an approximation register circuit 135. The approximation register circuit 135 is adapted to supply the digital approximation signal das to the digital-to-analogue converter 140 in response to the control signal ctrl of the transponder unit 200. The operation of the state machine 130 is controlled by a sensor control circuit 150, which receives the control signal ctrl from the transponder unit 200.

The transponder unit 200 comprises a transponder control circuit 210, which is adapted to supply the control signal ctrl to the implantable sensor unit 100 and the sensor control circuit 150. The transponder unit 200 further comprises a shadow state machine 230 including a shadow approximation register circuit 235. The shadow approximation register circuit 235 is adapted to generate a digital shadow approximation signal dsas identical to the digital approximation signal das on the basis of the control signal ctrl and the output signal comp of the comparator 120. The transponder unit 200 further comprises a clock circuit 220, which is adapted to supply a clock signal clk to the implantable sensor unit 100 and the transponder unit 200, wherein the clock signal clk is adapted to synchronize the approximation register circuit 135 of the implantable sensor unit 100 and the shadow approximation register circuit 235 of the transponder unit 200. The transponder unit 200 further comprises a processing circuit 240, which is adapted to determine digital sensor data from the digital shadow approximation signal dsas. The processing circuit 240 is connected to a transponder 250, which is adapted to transmit the digital sensor data to an external reader 400.

The wired connection 300 comprises at least two electrical lines, which are electrically isolated from each other to supply an operating voltage from the transponder unit 200 to the implantable sensor unit 100. According to the embodiment of FIG. 2, the control signal ctrl is an operating voltage of the implantable sensor unit 100, which is applied to the implantable sensor unit 100 via a first electrical line (ctrl) and a second electrical line (GND), which is held on ground potential GND. According to the embodiment of FIG. 2, the wired connection 300 thus comprises four electrical lines, wherein the third electrical line (clk) is used for transmitting the clock signal clk from the clock circuit 220 of the transponder unit 200 to the state machine 130 of the implantable sensor unit 100, and the fourth electrical line (comp) is used for transmitting the output signal comp of the comparator 120 to the shadow state machine 230 including the shadow approximation resistor circuit 235.

In the following, the operation of the sensor device 10 as shown in FIG. 2 will be described. When the transponder unit 200 switches the operation voltage on, the sensor unit 100 starts to perform an analogue-to-digital conversion process of the analogue signal output by the sensor 110. The analogue-to-digital conversion may be performed via a successive approximation analogue-to-digital conversion, by a tracking analogue-to-digital conversion, or by a predictive analogue-to-digital conversion.

By way of example, a state machine 130 performing a successive approximation analogue-to-digital conversion will be described hereinafter. If the control signal ctrl constituting the operating voltage is switched to an on-status, the approximation register circuit 135 of the state machine 130 and the shadow approximation register circuit 235 of the shadow state machine 230 are both initialized at the same time. The state machine 130 including the approximation register circuit 135 and the shadow state machine 230 including the shadow approximation register circuit 235 are further synchronized by the clock signal clk generated by the clock circuit 220. The successive approximation register is initialized so that the most significant bit is equal to a digital 1. This code is fed into the digital-to-analogue converter 140, which then supplies the analogue equivalent of this digital code, the analogue approximation signal approx, into the second input 120b of the comparator 120 for comparison with the analogue signal of the sensor 110 supplied to the first input 120a of the comparator 120. If the analogue signal of the sensor 110 exceeds the analogue approximation signal approx, the comparator 120 causes the state machine 130 and the approximation register circuit 135 to reset this bit. Otherwise, the bit is left at 1. Then, the next bit is set to 1 and the same test is done, continuing this binary search until every bit in the approximation register circuit 135 has been tested. The resulting code is the digital approximation signal dsas of the analogue signal of the sensor 110.

According to an embodiment, in case the sensor 110 is a capacitive sensor and the digital-to-analogue converter 140 is a programmable capacitor array, the analogue signal sens of the sensor 110 and the analogue approximation signal approx of the digital-to-analogue converter 140 are represented by respective charges on the respective capacitors. In this case the charges on the sensor capacitor of the sensor 110 and the ones on the programmable capacitor array of the digital-to-analogue converter 140 may also be subtracted and then compared to zero by the comparator 120. Thus, the comparator 120 may further comprise a subtractor adapted to subtract the signal on the second input 120b from the signal on the first input 120a, wherein the output signal of the subtractor is compared to zero signal (charge) within the comparator 120. The analogue signal sens of the sensor 110 and the analogue approximation signal approx of the digital-to-analogue converter 140 may also simply be added when providing charges of different signs. In this case, zero signal may be applied to the second terminal 120b, wherein both the analogue signal sens of the sensor 110 and the analogue approximation signal approx of the digital-to-analogue converter 140 are applied (and added) at the first terminal 120a of the comparator 120.

As can be seen from FIG. 2, the output signal comp of the comparator 120 is not only supplied to the state machine 130 and the approximation register circuit 135, but is also transmitted via the wired connection 300 to the shadow state machine 230 and the shadow approximation register circuit 235 of the transponder unit 200. Since the state machine 130 and the shadow state machine 230 are initialized at the same time and further synchronized by the same clock signal clk, and since both the state machine 130 and the shadow state machine 230 perform the same approximation process such as a successive approximation process, the shadow state machine 230 is adapted to set the state of the shadow approximation register circuit 235 in such a way that the approximation register circuit 135 and the shadow approximation register circuit 235 are in the same state by using the output signal comp of the comparator 120 supplied to both the state machine 130 and the shadow state machine 230.

Thus, the sensor device 10 makes use of an analogue-to-digital conversion process that approximates an analogue signal sens from a sensor 110 by an analogue approximation signal approx that is generated by the digital-to-analogue converter 140. The analogue approximation signal approx of the digital-to-analogue converter 140 is adjusted by the state machine 130 depending on the output signal comp of the comparator 120 that is adapted to compare the analogue signal sens of the sensor 110 with the analogue approximation signal approx of the digital-to-analogue converter 140. Depending on the state machine 130, the analogue-to-digital conversion process is a tracking analogue-to-digital conversion, a successive approximation analogue-to-digital conversion or a predictive analogue-to-digital conversion. In addition, a successive approximation analogue-to-digital conversion may be combined with a tracking analogue-to-digital conversion. Since a shadow state machine 230 is provided in the transponder unit 200, which is adapted to track the state of the approximation register circuit 135 by means of the output signal comp of the comparator 120, a complex interface may be avoided that allows to change configurations and deliver data according to a defined protocol. The transponder control circuit 210 delivers the supply voltage for the sensor unit 100, delivers the clock signal clk to the sensor unit 100 and receives the comparator 120 decision back, which is transmitted by the output signal comp of the comparator 120. Based on the comparator 120 feedback, the shadow state machine 230 performs the same operation as the state machine 130 of the sensor unit 100 and thus generates an identical value in the shadow approximation register 235 compared to the approximation register circuit 135. The content of the shadow approximation register circuit 235 being identical to that of the approximation register circuit 135 is output from the shadow approximation register circuit 235 as the digital shadow approximation signal dsas to the processing circuit 240. The processing circuit 240 may be adapted to supply directly the digital shadow approximation signal dsas to the transponder 250 to be transmitted to the external reader 400.

According to another embodiment, the processing circuit 240 may be adapted to determine a sensor value characteristic of the sensor 110 and to supply such digital sensor data to the transponder 250 to be transmitted to the external reader. In order to synchronize the state machine 130 and shadow state machine 230, the shadow state machine 230 resets its internal states when it turns on the supply of the sensor unit 100, wherein the sensor unit 100 does the same with its approximation register circuit 135 using a power on reset.

FIG. 3 is a digital timing diagram illustrating an analogue-to-digital conversion sequence of the analogue signal sens, output by the sensor 110, into the digital shadow approximation signal dsas, output by the shadow approximation register circuit 135. According to the embodiment as shown in FIG. 3, within an initialisation phase A, the conversion sequence starts with a sample initiated by the first clock followed by a successive approximation of an 8 bit value (16 clocks, which depends, however, on the hardware implementation). After this, within a fast tracking phase B, the 8 bit value that was found by the successive approximation is taken as a starting value for a tracking sequence with a new sample from the sensor 110 followed by three tracking steps to update the approximation value. The number of tracking steps per sensor sample can, however, be changed. The first tracking sequence is repeated four times and the output at each or each second or each fourth clock is delivered to the transponder unit 200 for further processing, such as low pass filtering, for example. After this initial fast tracking phase B, the state machine 130 changes into a different mode within a slow tracking phase C, and takes a new sensor sample followed again by three tracking steps and a longer gap until the next sample is acquired. In such a slow tracking mode, the shadow state machine 230 is adapted to decide when samples are taken by controlling the clock signal clk. Thus, it can change the sampling frequency without reconfiguration of the state machine 130 of the sensor unit 100. Of course the first fast tracking sequence within phase B could be omitted as well or the state machine 130 could continue in the fast tracking mode for a longer time period in order to acquire data with a maximum resolution. Of course the number of tracking steps after each sensor sample can be changed and adapted to application requirements. Thus, the implantable sensor unit 100 may be adapted to take a new sample of the sensor signal sens at the beginning of each successive conversion cycle and after a defined number of tracking steps.

To avoid metastability problems of the comparator 120, a single storage of the approximation register circuit 135 is provided if the shadow approximation register circuit 235 shall not have a different entry due to metastable decisions of the comparator 120. This can be ensured by various minor modifications, such as providing a flip flop at the output of the integrated circuit that is in the loop of the successive approximation register conversion or alternatively a serial data stream of the approximation register entry may be send out with a latency of at least one clock period and send out the bit that was updated last in the conversions sequence. Thus, as can be seen in the phase C of FIG. 3, the transponder unit 200 may be adapted to interrupt the operation of the approximation register circuit 135 and the shadow approximation register circuit 235 by interrupting the clock signal clk.

Thus, the sensor device 10 is adapted to digitally approximate a sampled value of the sensor 110 using a state machine 130, a digital-to-analogue converter 140 and a comparator 120 (similar to the hardware of successive approximation register, tracking or predictive analogue-to-digital converter). The sensor unit 100 is a remote device and the state machine 130 is completely or partly copied on the transponder unit 200 in order to reproduce the approximated value based on the comparator feedback of the comparator 120 (the signal comp) that is derived from the comparator decision as it is delivered from the sensor unit 100. It further switches from an initial successive approximation into a tracking mode in order to be able to follow a slow signal with a minimum number of clock cycles in order to save power. Thus, the implantable sensor unit 100 may be configured to switch from a successive approximation mode into a tracking mode after a predefined number of clock cycles of the clock signal clk. Furthermore, the output signal comp of the comparator 120 may be stored in an intermediate storage of the state machine 130 to be transmitted to the shadow state machine 230, instead of transmitting the output signal comp of the comparator 120 directly from the comparator 120 to the shadow approximation register circuit 235.

The transponder 250 may comprise at least one of a radio frequency identification (RFID)/nearfield communication (NFC) antenna and a radio frequency identification (RFID)/ultra-high frequency (UHF) antenna, to transmit the digital sensor data supplied by the processing circuit 240 to the external reader 400.

RFID devices operate at different radio frequency ranges, e.g. low frequency (LF) at about 28 to 135 kHz, high frequency (HF) at about 13.56 MHz, and ultra-high frequency (UHF) at 860 to 960 MHz. Each frequency range has unique characteristic in terms of RFID performance.

NFC is a short range technology that enables two devices to communicate when they are brought into actual touching distance. NFC enables sharing power and data using magnetic field induction at 13.56 MHz (HF) band, at short range, supporting varying data rates from 106 kbps, 212 kbps to 424 kbps. A key feature of NFC is that is allows two devices to interconnect. In reader/writer mode, an NFC tag is a passive device that stores data that can be read by an NFC enable device. In peer-to-peer mode, two NFC devices can exchange data. Bluetooth or WiFi link set up parameters can be shared using NFC and data such as virtual business cards or digital photos can be exchanged. In card emulation mode, the NFC device itself acts as an NFC tag, appearing to an external interrogator as a traditional contact less smart card. These NFC standards are acknowledged by major standardisation bodies and based on ISO/IEC 18092.

Passive UHF systems use propagation coupling, where an interrogator antenna emits electromagnetic energy radio frequency waves and the RFID tag receives the energy from the interrogator antenna, and the integrated circuit uses the energy to change the load on the antenna and reflect back an altered signal that is then demodulated. For the LF and HF RFID systems using interactive coupling, the range of the interrogator field is small (0.2 to 80 cm) and can be relatively easily controlled. UHF systems that use propagation coupling are harder to control, because energy is sent over long distances. The radio waves can reflect on hard surfaces and reach tags that are not in the normal range. LF and HF systems perform better than UHF systems around metal and water. The radio waves do reflect off metal and cause false reads, and they are better able to penetrate water. UHF radio waves are attenuated by water. In addition, communication may be performed via any one of an Industrial, Scientific and Medical (ISM) Band, which operates in a frequency range between 6.765 MHz to 246 GHz and has bandwidths of up to 2 GHz. The transponder 250 may further comprise an energy harvesting unit to harvest electromagnetic energy received by the radio frequency identification (RFID)/near-field communication (NFC) antenna, for example, which is transmitted by the external reader 400.

FIGS. 4A and 4B are schematic cross-sectional views of a sensor unit 100 according to one or more embodiments before and after insertion into a vessel end of a vessel 600. As can be seen from FIGS. 4A and 4B, the sensor unit 100 may be an integrated semiconductor circuit, which comprises a proximal part 101 plugging an end portion 510 of a tubular body 500 and having an interconnection side 102, and a distal part 103 protruding from the end portion 510 of the tubular body 500 and having a sensor side 104.

The tubular body 500 may comprise a rigid or stiff material (having an elastic module of higher than 1 kN/mm$^2$) or a flexible material (having an elastic module of lower than 1 kN/mm$^2$). The end portion 510 may comprise a different material than the remaining tubular body 500. The end portion 510 may comprise, for example, a rigid material such as glass, metal (e.g. titanium), silicon or a biocompatible material, wherein the remaining tubular body 500 may comprise a flexible material such as a synthetic material. The synthetic material may comprise PET, PI, or silicone. A seal junction between the open vessel end 610 and the end portion 510 of the tubular body 500 may be formed by clamping, by suture or by tying. The seal junction may be formed by pressing the tissue of the vessel 600 against the outer wall of the tubular body 500 by a tie or by a clamping device. Herein, all methods for connecting an open vessel end 610 with a tubular body 500, which are known in the surgical field, shall be included for forming the seal junction between the end portion 510 and the open vessel 610.

The sensor unit 100 may be semiconductor device, in which the sensor 110 is integrated. The sensor 110 may, for example, be a semiconductor pressure sensor. One example of a semiconductor pressure sensor may be MEMS-based pressure sensor integrated in a semiconductor die. In a MEMS-based pressure sensor, a polysilicon membrane covers a vacuum chamber in a semiconductor body, wherein the deflection of the polysilicon membrane relative to the semiconductor body may be measured positively by a piezoelectric effect. Thus, the sensor 110 may comprise a pressure sensor adapted to sense a blood pressure within the vessel 600. According to an embodiment, the vessel 600 may be a carotid artery of a rodent. The rodent may be a mouse. The implantable sensor unit 100 thus allows an accurate monitoring of a blood pressure of a lab mouse with a sampling rate that allows to monitor the blood pressure transient over the heartbeat cycle instead of measuring just an average. Therefore, the micro-machined semiconductor pressure sensor of the sensor 110 is directly in contact with the blood in the vessel 600 instead of using pressure sensors connected to the vessel 600 via a fluid filled tube of at least a few centimeter length.

As can be further seen from FIGS. 4A and 4B, the sensor unit 100 may be inserted into the open vessel end 610, wherein the vessel end 610 is sealed by the implantable sensor unit 100 plugging the vessel 600 without further clamping or tying. If necessary, the vessel 600 may be sealed by additional surgical measures as by clamping or tying. The implantable sensor unit 100 may be shaped in a geometry which simplifies the implantation into the vessel 600 as well as the forming a seal junction. In order to simplify the implantation process, the implantable sensor unit 100 comprising the semiconductor die may have a circular shape along a cross-sectional area at the distal part 103 or at the end portion 510 of the tubular body 500. Furthermore, the implantable sensor unit 100 may have rounded edges at the distal part 103. The rounded edges may be manufactured by depositing a photoresist onto the sensor side 104 of the semiconductor body of the implantable sensor unit 100 (excluding the area, on which the sensor 110 is provided, comprising an active pressure sensing area) and partly removing the material at the edge, e.g. by variation of the development process. Thereafter, material is partly removed from the edge of the semiconductor body of the implantable sensor unit 100 using appropriate plasma treatments, e.g. with varying mask diameters.

The implantable sensor unit 100 being an integrated semiconductor circuit may have a volume in a range between 0.1 $mm^3$ to 20 $mm^3$. The sensor 110 may further comprise at least one of a temperature sensor, an electrocardiogram sensor, an electroencephalogram sensor, a chemical sensor, a blood flow sensor, and a biochemical sensor.

The wired connection 300 may have a maximum diameter of 5 mm and a length in a range of 1 mm to 50 mm. Furthermore, the wired connection 300 flexibly connects the sensor unit 100 and the transponder unit 200. As shown in FIG. 4B, the wired connection 300 may have a coax cable structure. Herein, a contiguous wiring layer 320 may be provided at the inner side of the tubular body 500, wherein an inner wiring structure 310 comprising at least one electrical line may be guided through the tubular body 500 to interconnect the implantable sensor unit 100 and the transponder unit 200. The inner wiring structure 310 and the contiguous wiring layer 320 form a coax cable structure inside the tubular body 500. In this case, the ground signal GND as shown in FIG. 2 may be transmitted via the contiguous wiring layer 320 to shield the inner wiring structure 310 from external interferences. However, the wired connection 300 may also be provided as a cable having a multitude of wires or as a microwire structure without using the tubular body 500, for transmitting a signal between the transponder unit 200 and the sensor unit 100. For example, the tubular body 500 may be used only for inserting the sensor unit 100 into the open vessel end 610 of the vessel 600, wherein the wired connection 300 is extended beyond the proximal end of the tubular body 500 to be connected with the transponder unit 200. Thus, the sensor unit 100 and the transponder unit 200 are provided as separate units, which are connected by a cable connection by means of the wired connection 300.

Figure 5:
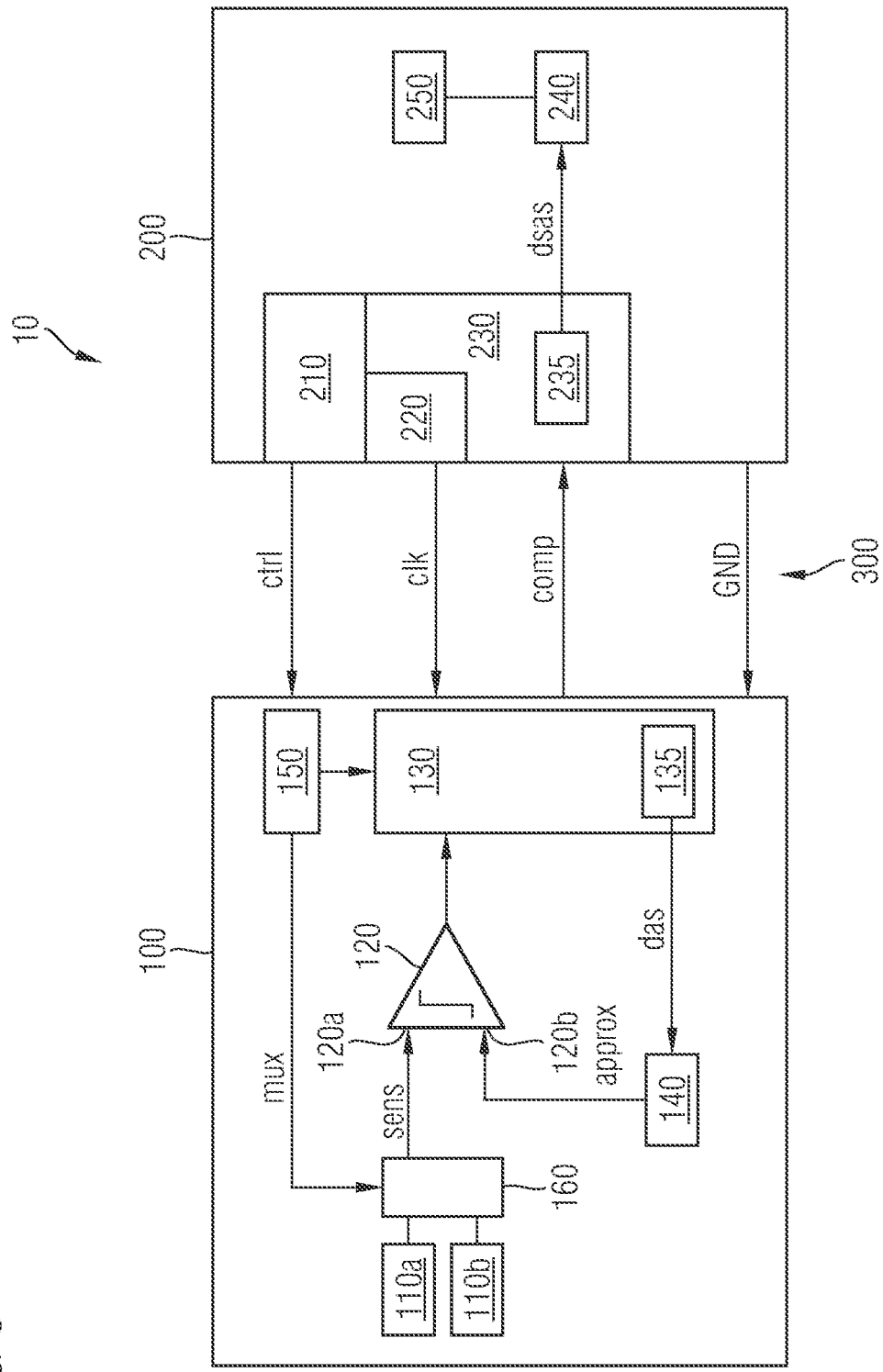
FIG. 5 is a schematic block diagram of a sensor device according to one or more embodiments.

FIG. 5 is a schematic block circuit diagram of a sensor device 10 according to one or more embodiments. As can be seen from FIG. 5, the sensor unit 100 includes a multiplexer circuit 160 to selectively connect at least two sensors 110*a*, 110*b* with the first input 120*a* of the comparator 120. The sensor 110*a* may be a pressure sensor, wherein the sensor 110*b* may be a temperature sensor. Thus, the sensor unit 100 is adapted to multiplex between the output signals of the sensors 110*a*, 110*b* and to supply the multiplexed analogue signal of one of the sensors 110*a*, 110*b* to the first input 120*a* of the comparator 120. The multiplexer circuit 160 may be controlled by the sensor control circuit 150 via a multiplexer control signal mux. The measurement sequence may start with the temperature sample and a successive approximation to evaluate the temperature sample of the sensor 110*b* being a temperature sensor. Afterwards the sensor device 10 takes the first pressure sample and performs a second successive approximation and then switches to a tracking mode for the sensor 110*a* being a pressure sensor. The next temperature sample would be taken after a power down in this case which is under the control of the shadow state machine 230. Alternatively each, for example a next temperature sample could be inserted after a predefined number of tracking steps which is known to the state machine 130 as well as the shadow state machine 230.

The characteristic frequency of pressure variation to be measured by the sensor 110*a* being a pressure sensor, e.g. a blood pressure sensor, may be in a range between 10 to 20 Hz. The clock rate of the clock signal clk may be in a range between 500 kHz to 2 MHz. Thus, the ratio of the clock rate of a clock signal clk and the characteristic frequency of pressure variation, for example within a vessel, is very high. The characteristic time of temperature variation is in a range of 100 seconds. Thus, the analogue signal of the sensor 110*b* being a temperature sensor has to be converted into a digital shadow approximation with a repetition rate in the range between every 10 seconds to every 100 seconds. The output signal of the sensor 110*a* being a pressure sensor may be converted into the digital shadow approximation signal dsas with a repetition rate between 50 Hz to 2000 Hz. In view of the clock rate of the clock signal clk of about 1 MHz, a multitude of sensors 110 may be multiplexed and read out, wherein the respective sensor data is sequentially transmitted from the transponder 250 to the external reader 400.

Figure 6:
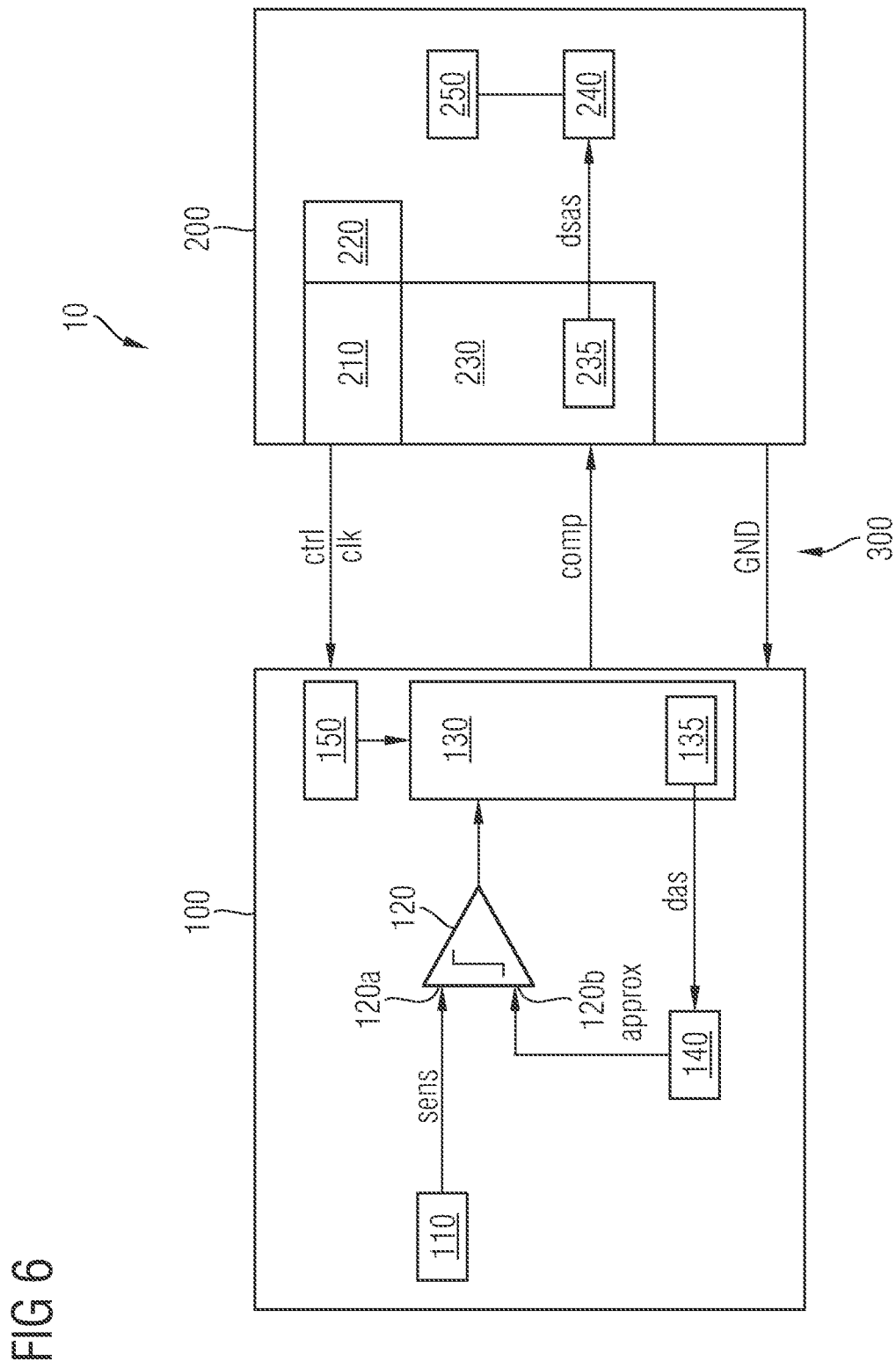
FIG. 6 is a schematic block diagram of a sensor device according to one or more embodiments.

FIG. 6 is a schematic block diagram of a sensor device 10 according to one or more embodiments. As can be seen from FIG. 6, the transponder unit 200 comprises the clock circuit 220, wherein the transponder unit 200 is adapted to supply the clock signal clk to the implantable sensor unit 100 via a modulated operating voltage (which further constitutes the control signal ctrl). By transmitting the clock signal clk and the control signal ctrl as a modulated operating voltage via the same electrical line (ctrl/clk), the number of electrical lines of the wired connection 300 may be reduced by one. The clock signal clk may be transmitted by a modulation of the supply voltage e.g. switched between 1.5 V and 2 V. On the side of the sensor unit 100, the clock signal clk is extracted in the sensor control signal 150, by using a comparator, for example.

Figure 7:
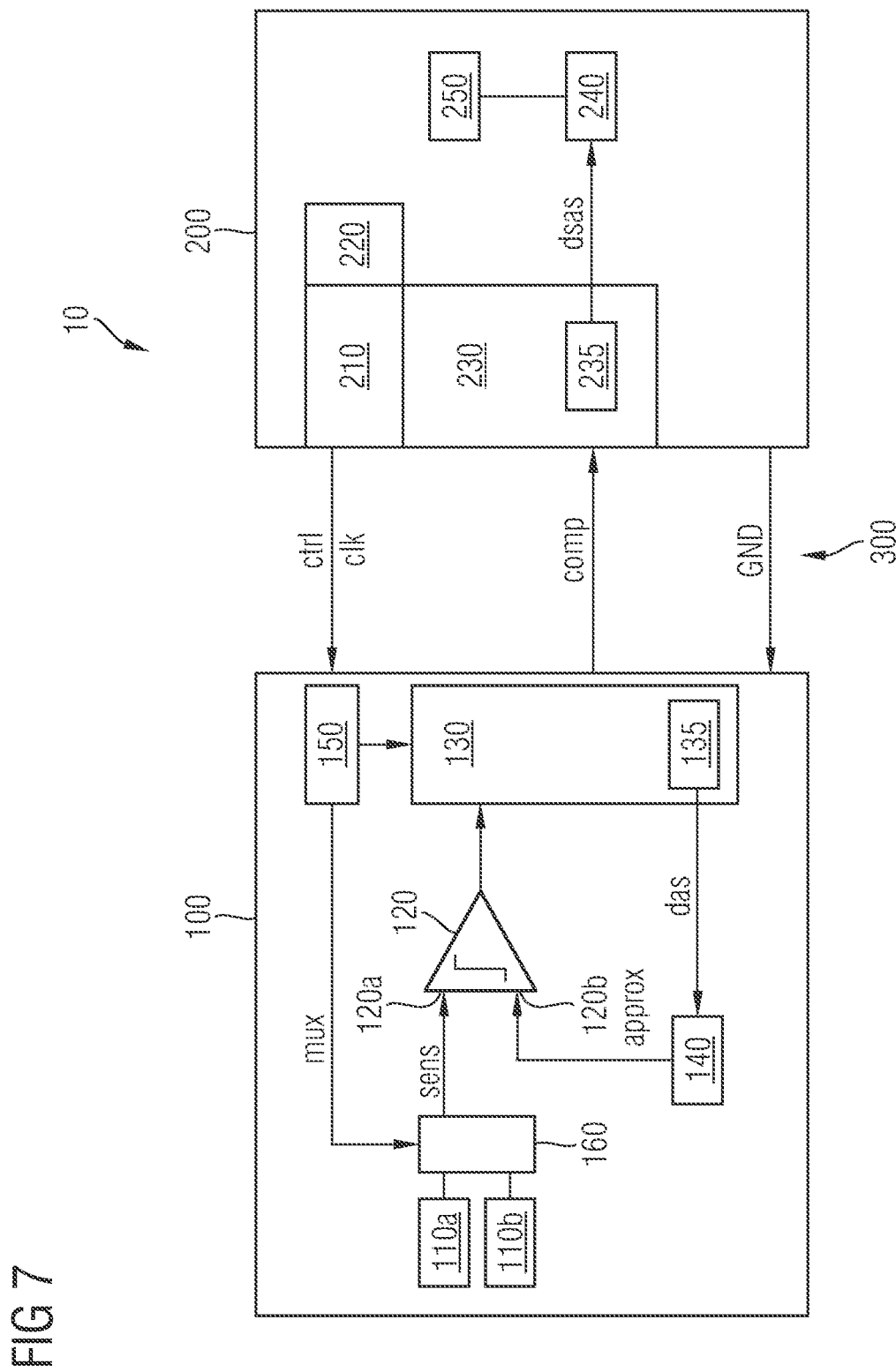
FIG. 7 is a schematic block diagram of a sensor device according to one or more embodiments.

FIG. 7 is a schematic block diagram of a sensor device 10, in which a multiplexer circuit 160 is provided as already shown and described with regard to the embodiment of FIG. 5, wherein the transponder unit 200 is adapted to supply the clock signal clk to the implantable sensor unit 100 via a modulated operating voltage, as shown and described with regard to the embodiment of FIG. 6.

Figure 8:
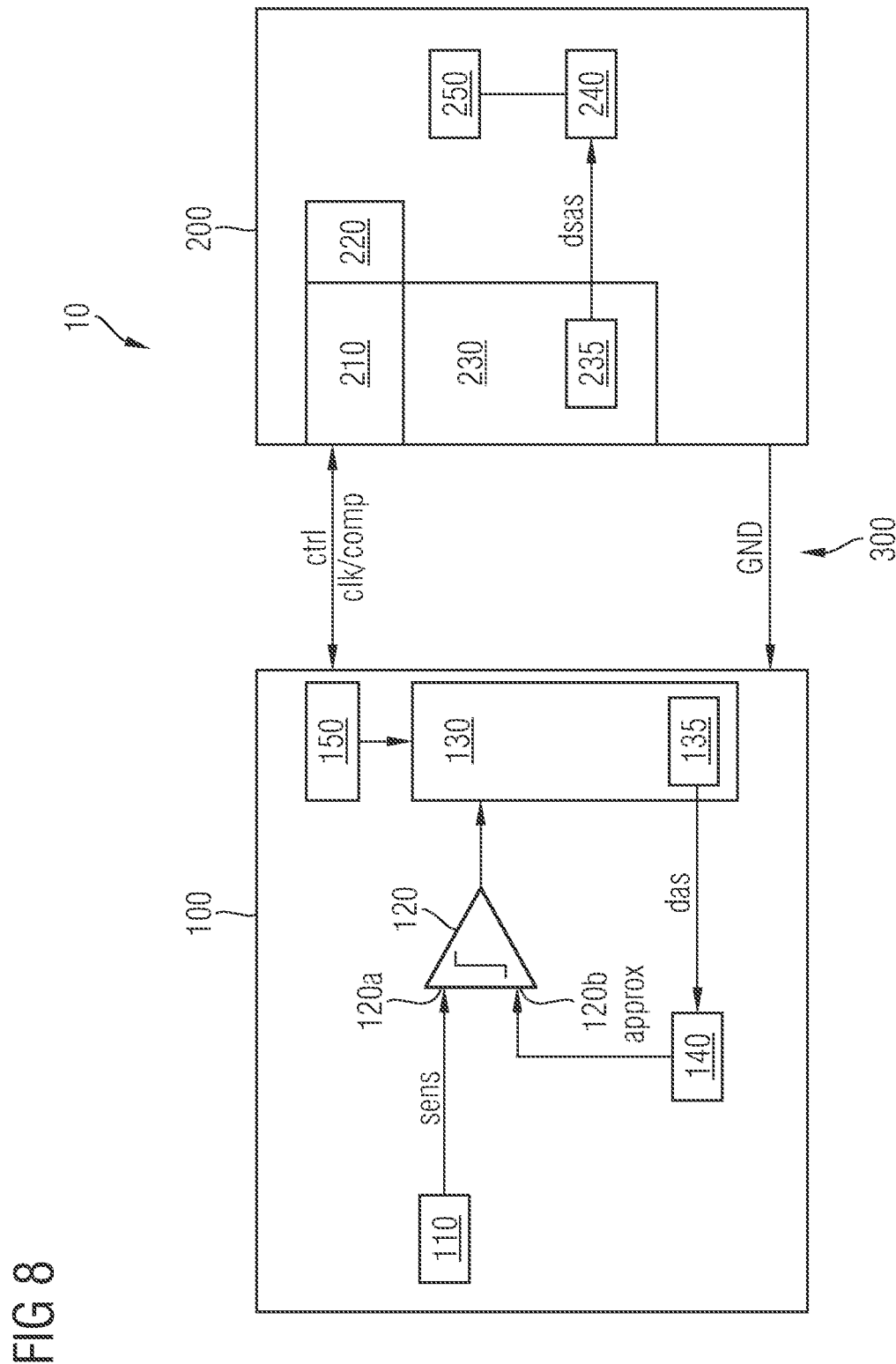
FIG. 8 is a schematic block diagram of a sensor device according to one or more embodiments.

FIG. 8 is a schematic block diagram of a sensor device 10 according to one or more embodiments. As shown in FIG. 8, the electrical line for transmitting the output signal comp of the comparator 120 of the wired connection 300 is omitted, wherein the output signal comp of the comparator 120 is modulated onto the supply current. This could be statically for the next clock phase, e.g. low is the idle current of the sensor die (which may be below 1 µA when the comparison of the sensor value and the approximated DAC output is finished) and high is the idle current plus an offset of e.g. 2 µA. Of course the static increase of the supply current could be replaced by a current pulse in a certain distance from a clock edge, e.g. low being 200 ns pulse after 100 ns, and high being 100 ns pulse after 200 ns. Thus, the implantable sensor unit 100 is adapted to supply the output signal comp of the comparator 120 to the transponder unit 200 via a modulated operating current. According to another embodiments, a clock for the analogue-to-digital converter 140 of the sensor unit 100 may be used that is divided down from a higher clock that is delivered by the transponder unit 200 and the response may be sent out with a delay of a defined number of the faster master clock cycles or other information interleaved between the sensor data may be transmitted or the sensor data bits may be repeated several times to improve the reliability of the communication.

Figure 9:
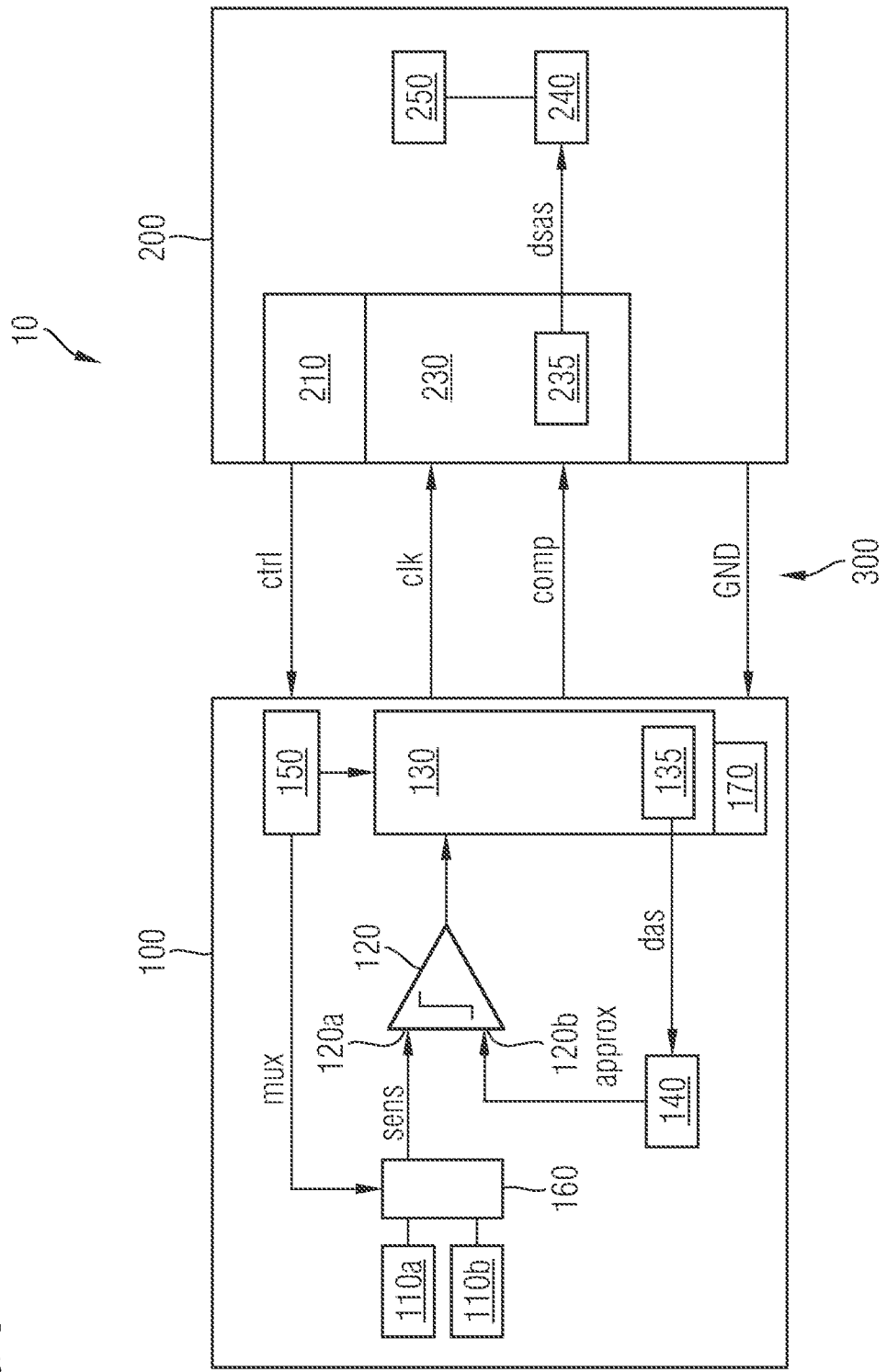
FIG. 9 is a schematic block diagram of a sensor device according to one or more embodiments.

FIG. 9 is a schematic block diagram of a sensor device 10 according to one or more embodiments. As can be seen from FIG. 9, the implantable sensor unit 100 comprises the clock circuit 170, wherein the implantable sensor unit 100 is adapted to supply the clock signal clk to the transponder unit 200. Thus, the sensor unit 100 may include a local oscillator in the clock circuit 170 that generates the clock frequency for the state machine 130 and delivers this clock clk to the shadow state machine 230. For the case that this oscillator is temperature-dependent, the delivered clock frequency may be used as a temperature sensor signal as well without the need to multiplex between pressure and temperature sensor.

Figure 10:
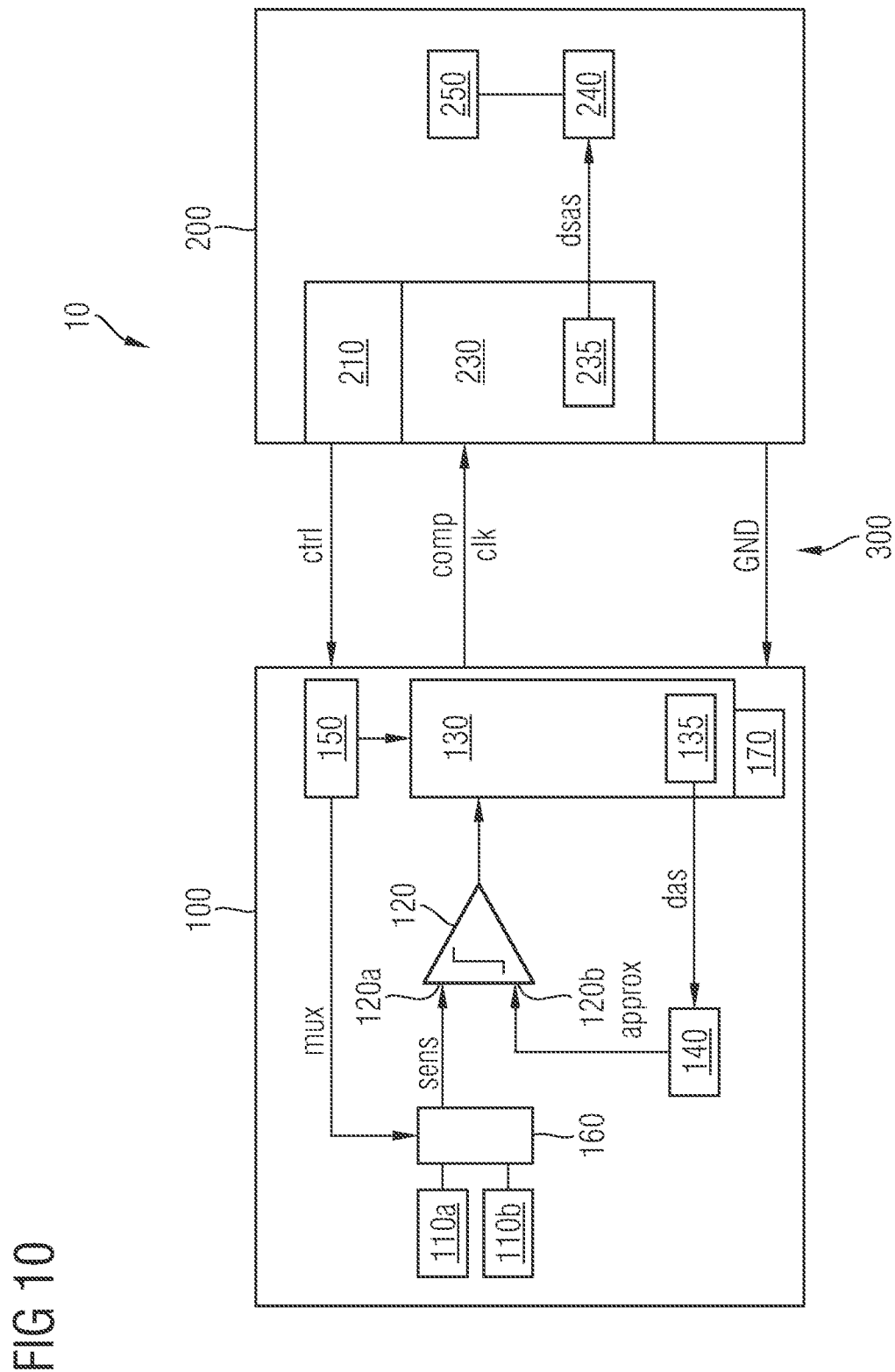
FIG. 10 is a schematic block diagram of a sensor device according to one or more embodiments.

FIG. 10 is a schematic block diagram of a sensor device 10 according to one or more embodiments. As can be seen from FIG. 10, the implantable sensor unit 100 is adapted to supply the clock signal clk to the transponder unit 200 via a modulated output signal comp of the comparator 120. Herein, the output signal comp of the comparator 120 and the clock signal clk may be transmitted via only one common electrical line (comp/clk) of the wired connection 300, thus reducing the number of wires of the wired connection 300. As a result, the data and clock line could alternatively be combined if the delivered signals that are derived from the comparator decisions are delivered encoded in a form that allows to extract the clock frequency from the message. According to an embodiment, the modulated output signal comp of the comparator 120 may be a Manchester code signal. In other words, the output signal comp of the comparator 120 and the clock signal clk are combined to one signal by a Manchester coding process. Manchester coding, also known as phase encoding, is a line code in which the encoding of each data bit has at least one transition and occupies the same time. It therefore has no DC component, and is self-clocking, which means that it may be inductively or capacitively coupled, and that a clock signal can be recovered from the encoded data.

Although specific embodiments have been illustrated and described herein, it will be appreciated by those of ordinary skill in the art that a variety of alternate and/or equivalent implementations may be substituted for the specific embodiments shown and described without departing from the scope of the general inventive concept. This application is intended to cover any adaptations or variations of the specific embodiments discussed herein. Therefore, it is intended to be limited only by the claims and the equivalents thereof.

What is claimed is:

1. A sensor device, comprising:
an implantable sensor unit adapted to be implanted into a body, the implantable sensor unit comprising a comparator and a pressure sensor adapted to sense a characteristic of the body in vivo, the pressure sensor being further adapted to supply an analogue signal to a first input of the comparator;
a transponder unit adapted to supply a control signal to the implantable sensor unit and to receive an output signal of the comparator, the implantable sensor unit being adapted to supply an analogue approximation signal to a second input of the comparator in response to the control signal; and
a wired connection flexibly and electrically connecting the implantable sensor unit and the transponder unit, the wired connection being adapted to transmit the control signal and the output signal of the comparator.

2. The sensor device of claim 1, wherein the wired connection comprises at least two electrical lines electrically isolated from each other to supply an operating voltage from the transponder unit to the implantable sensor unit.

3. The sensor device of claim 2, wherein the control signal is the operating voltage.

4. The sensor device of claim 1, wherein the wired connection has a maximum diameter of 5 mm and a length in a range of 1 mm to 50 mm.

5. The sensor device of claim 1, wherein the pressure sensor is adapted to sense a blood pressure within a vessel.

6. The sensor device of claim 5, wherein the vessel is a carotid artery of a rodent.

7. The sensor device of claim 1, wherein the implantable sensor unit is an integrated semiconductor circuit having a volume in a range between 0.1 $mm^3$ to 20 $mm^3$.

8. The sensor device of claim 1, wherein the implantable sensor unit further comprises at least one of a temperature sensor, an electrocardiogram sensor, an electroencephalogram sensor, a blood flow sensor, a chemical sensor, and a biochemical sensor.

9. The sensor device of claim 1, wherein the implantable sensor unit comprises a multiplexer circuit to selectively connect at least two sensors with the first input of the comparator.

10. The sensor device of claim 1, wherein the implantable sensor unit is adapted to supply the output signal of the comparator to the transponder unit via a modulated operating current.

11. The sensor device of claim 1, wherein the implantable sensor unit further comprises:
a digital-to-analogue converter adapted to supply the analogue approximation signal to the second input of the comparator based on a digital approximation signal; and
an approximation register circuit adapted to supply the digital approximation signal to the digital-to-analogue converter in response to the control signal of the transponder unit.

12. The sensor device of claim 11, wherein the transponder unit comprises:
a transponder control circuit adapted to supply the control signal to the implantable sensor unit; and
a shadow approximation register circuit adapted to generate a digital shadow approximation signal identical to the digital approximation signal on the basis of the control signal and the output signal of the comparator.

13. The sensor device of claim 12, wherein the control signal is adapted to initialize the approximation register circuit and the shadow approximation register circuit.

14. The sensor device of claim 12, wherein the transponder unit further comprises:
a processing circuit adapted to determine digital sensor data from the digital shadow approximation signal; and
a transponder adapted to transmit the digital sensor data to an external reader.

15. The sensor device of claim 12, further comprising:
a clock circuit adapted to supply a clock signal to the implantable sensor unit and the transponder unit, the clock signal being adapted to synchronize the approximation register circuit and the shadow approximation register circuit.

16. The sensor device of claim 15, wherein the implantable sensor unit is configured to switch from a successive approximation mode into a tracking mode after a predefined number of clock cycles of the clock signal.

17. The sensor device of claim 15, wherein the implantable sensor unit is adapted to take a new sample of the analogue signal at a beginning of each successive conversion cycle and after a defined number of tracking steps.

18. The sensor device of claim 15, wherein the transponder unit comprises the clock circuit, the transponder unit being adapted to interrupt an operation of the approximation register circuit and the shadow approximation register circuit by interrupting the clock signal.

19. The sensor device of claim 15, wherein the transponder unit comprises the clock circuit, the transponder unit being adapted to supply the clock signal to the implantable sensor unit via a modulated operating voltage.

20. The sensor device of claim 15, wherein the implantable sensor unit comprises the clock circuit, the implantable sensor unit being adapted to supply the clock signal to the transponder unit.

21. The sensor device of claim 20, the implantable sensor unit is adapted to supply the clock signal to the transponder unit via a modulated output signal of the comparator.

22. The sensor device of claim 21, wherein the modulated output signal of the comparator is a Manchester Code Signal.

* * * * *